(12) United States Patent
Daidoji et al.

(10) Patent No.: US 9,880,380 B2
(45) Date of Patent: Jan. 30, 2018

(54) ENDOSCOPE SYSTEM

(71) Applicant: OLYMPUS CORPORATION, Tokyo (JP)

(72) Inventors: Bakusui Daidoji, Hachioji (JP); Takeshi Ito, Hino (JP); Satoshi Ohara, Hachioji (JP); Motoki Tabata, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/350,181

(22) Filed: Nov. 14, 2016

(65) Prior Publication Data

US 2017/0059849 A1    Mar. 2, 2017

Related U.S. Application Data

(63) Continuation of application No. PCT/JP2015/062999, filed on Apr. 30, 2015.

(30) Foreign Application Priority Data

May 14, 2014    (JP) ................................. 2014-100841

(51) Int. Cl.
*A61B 1/04*    (2006.01)
*G02B 23/24*    (2006.01)
(Continued)

(52) U.S. Cl.
CPC ...... *G02B 23/2469* (2013.01); *A61B 1/00045* (2013.01); *A61B 1/04* (2013.01);
(Continued)

(58) Field of Classification Search
CPC ...................................... A61B 1/04
(Continued)

(56) References Cited

U.S. PATENT DOCUMENTS

2009/0002794 A1*    1/2009    Weir .................. A61B 1/00096
359/213.1
2012/0053420 A1*    3/2012    Kasamatsu .......... A61B 1/0638
600/182
(Continued)

FOREIGN PATENT DOCUMENTS

CN            103505174 A        1/2014
JP            2002-065602 A      3/2002
(Continued)

OTHER PUBLICATIONS

International Search Report dated Jul. 28, 2015 issued in PCT/JP2015/062999.*
(Continued)

*Primary Examiner* — Clayton E Laballe
*Assistant Examiner* — Kevin Butler
(74) *Attorney, Agent, or Firm* — Scully, Scott, Murphy & Presser, PC

(57) ABSTRACT

An endoscope system has observation modes making observations with lights having optical characteristics different from each other. The system includes an endoscope including an insertion section provided with an illumination window, a light guide arranged in the insertion section, and including an entrance end on which the lights enter and a plurality of light guide areas that guide the lights entered on the entrance end, and an entrance area switching unit that switches between the light guide areas through which the entered lights are guided by switching between areas on which the lights enter at the entrance end in accordance with an observation mode.

26 Claims, 11 Drawing Sheets

(51) Int. Cl.

| | | |
|---|---|---|
| *A61B 1/00* | (2006.01) | |
| *A61B 1/07* | (2006.01) | |
| *G02B 6/02* | (2006.01) | |
| *G02B 6/036* | (2006.01) | |
| *G02B 6/04* | (2006.01) | |
| *G02B 6/293* | (2006.01) | |
| *G02B 6/35* | (2006.01) | |
| *G02B 6/42* | (2006.01) | |
| *G02B 6/44* | (2006.01) | |
| *G02B 27/48* | (2006.01) | |
| *A61B 1/06* | (2006.01) | |
| *G02B 6/32* | (2006.01) | |
| *G02B 26/08* | (2006.01) | |
| *G02B 6/26* | (2006.01) | |

(52) U.S. Cl.
CPC .............. *A61B 1/0638* (2013.01); *A61B 1/07* (2013.01); *G02B 6/02042* (2013.01); *G02B 6/036* (2013.01); *G02B 6/04* (2013.01); *G02B 6/29388* (2013.01); *G02B 6/3506* (2013.01); *G02B 6/3598* (2013.01); *G02B 6/4268* (2013.01); *G02B 6/4471* (2013.01); *G02B 23/2461* (2013.01); *G02B 23/2484* (2013.01); *G02B 27/48* (2013.01); *A61B 1/00163* (2013.01); *A61B 1/06* (2013.01); *G02B 6/26* (2013.01); *G02B 6/32* (2013.01); *G02B 26/0875* (2013.01)

(58) Field of Classification Search
USPC ............................................ 396/27; 600/101
See application file for complete search history.

(56) References Cited

U.S. PATENT DOCUMENTS

| | | | | |
|---|---|---|---|---|
| 2012/0083656 | A1* | 4/2012 | Kuroda .............. | A61B 1/00096 600/165 |
| 2013/0345517 | A1 | 12/2013 | Morimoto et al. | |
| 2016/0242626 | A1* | 8/2016 | Daidoji .............. | A61B 1/00002 |
| 2017/0059849 | A1* | 3/2017 | Daidoji .................... | A61B 1/00 |

FOREIGN PATENT DOCUMENTS

| | | | | | |
|---|---|---|---|---|---|
| JP | 2002065602 | * | 5/2002 | .............. | A61B 1/00 |
| JP | 2002-336196 A | | 11/2002 | | |
| JP | 2002336196 | * | 11/2002 | .............. | A61B 1/03 |
| JP | 2004-512538 A | | 4/2004 | | |

OTHER PUBLICATIONS

Written Opinion of ISR dated May 14, 2014 issued in PCT/JP2015/062999.*

English translation of International Preliminary Report on Patentability dated Nov. 24, 2016 together with the Written Opinion received in related International Application No. PCT/JP2015/062999.

English abstract of WO 2002/036015 A1 dated May 10, 2002.

Chinese Office Action dated Aug. 16, 2017 in Chinese Patent Application No. 201580024678.6.

\* cited by examiner

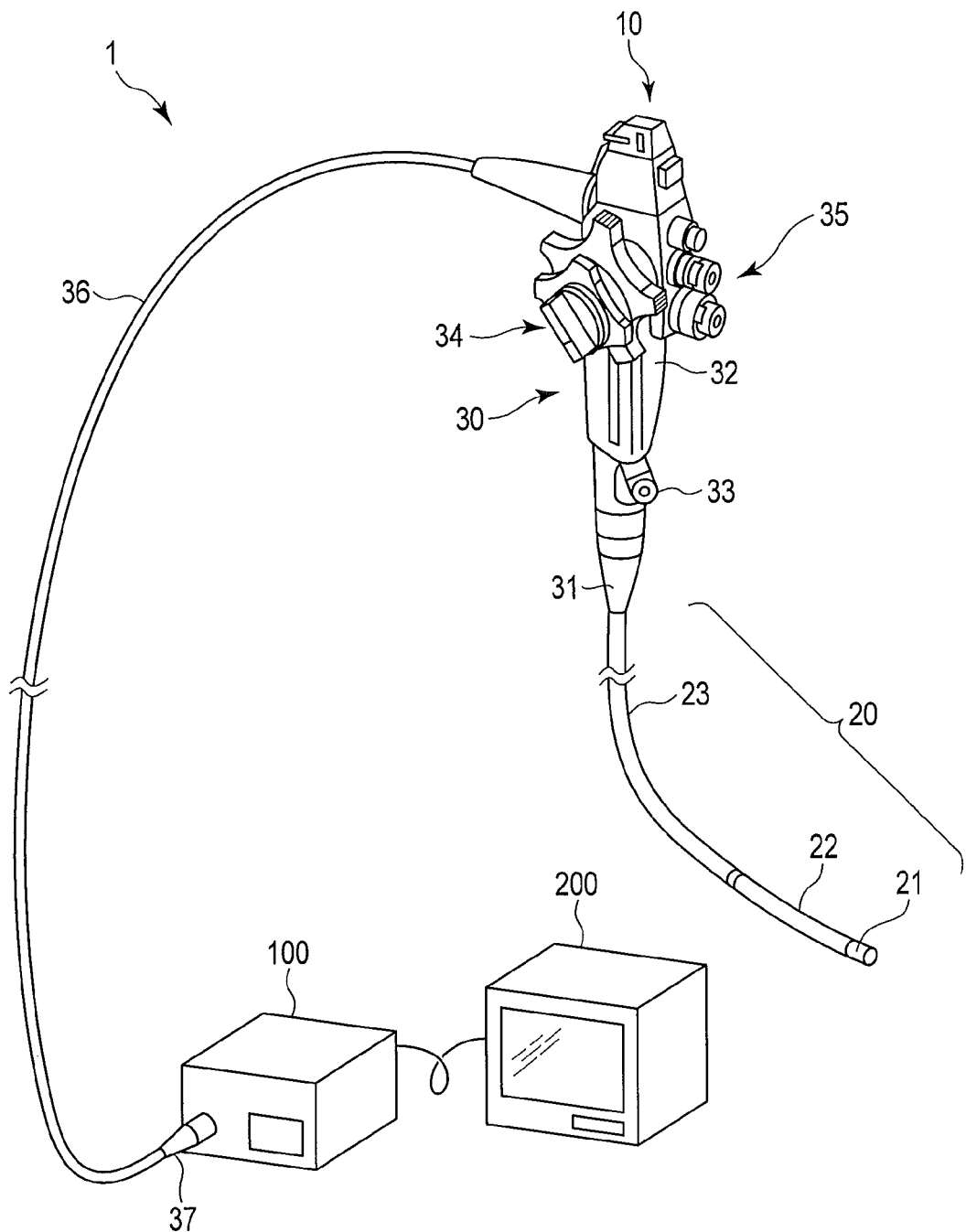
F I G. 1

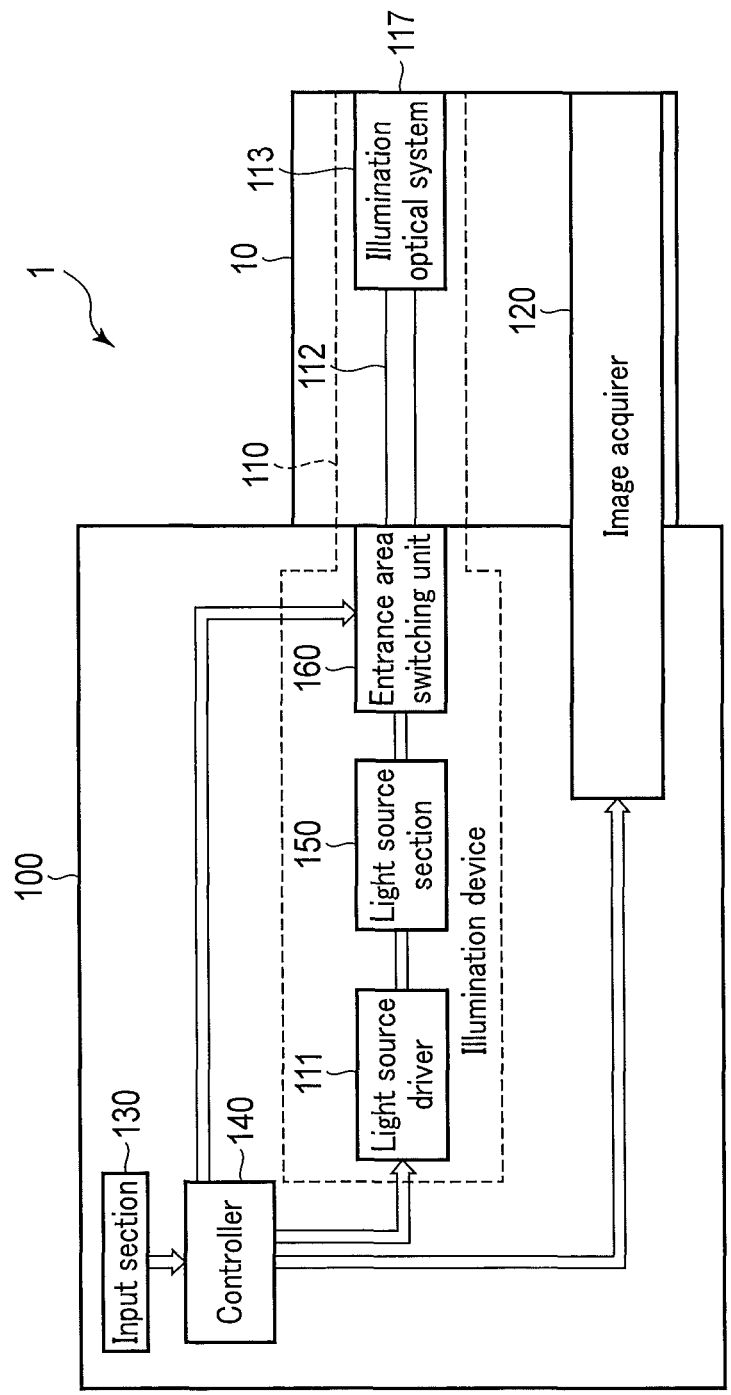
F I G. 2

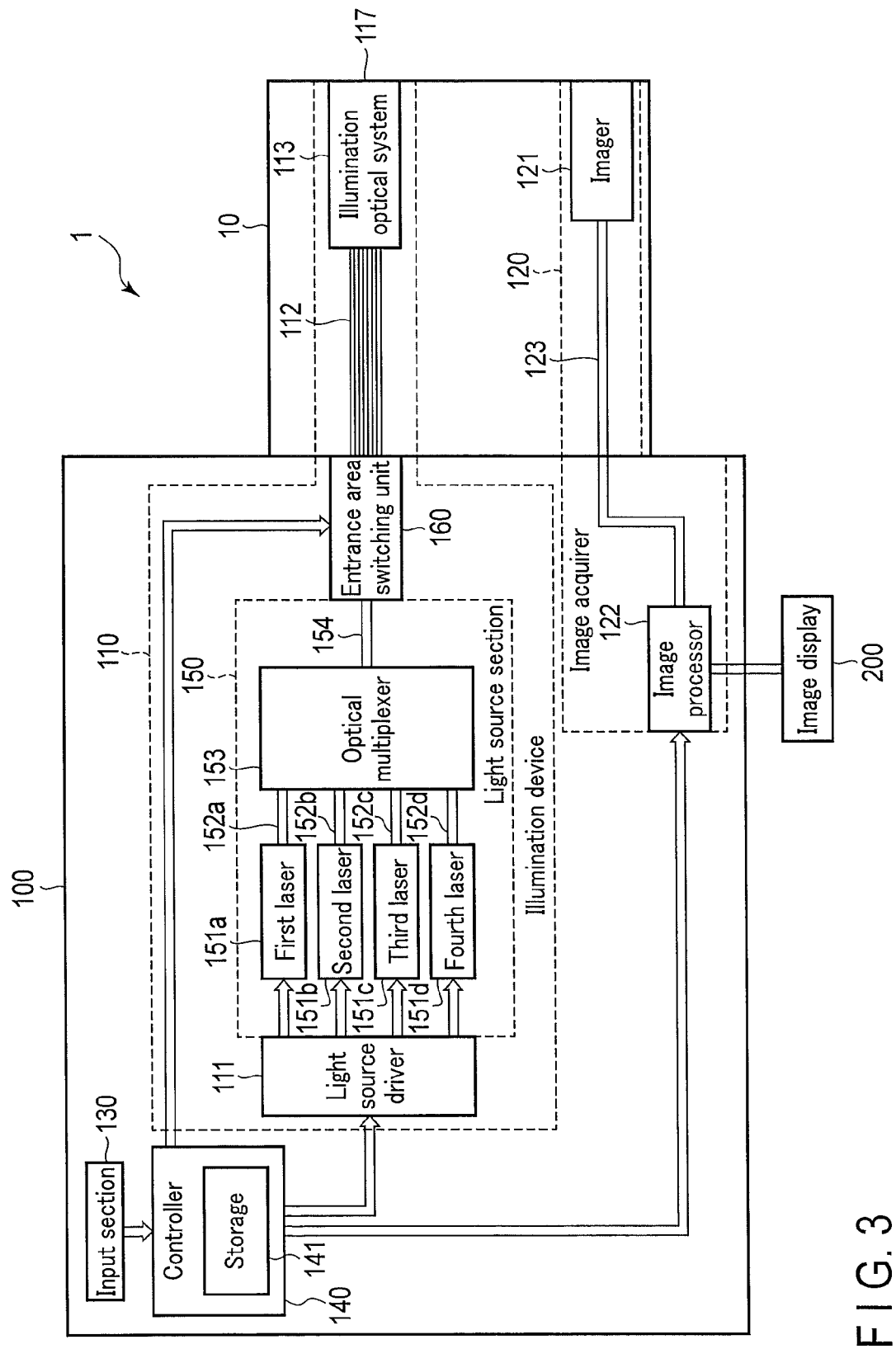
F I G. 3

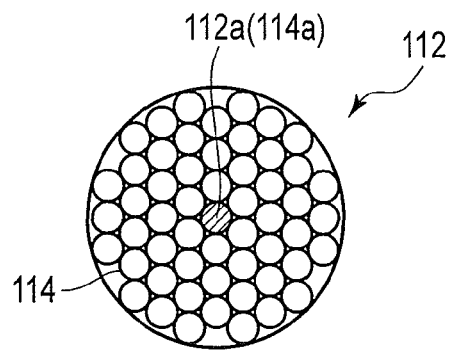
F I G. 4a
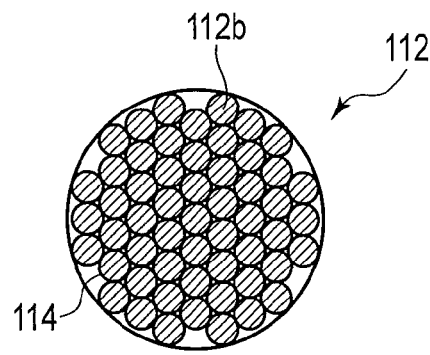
F I G. 4b
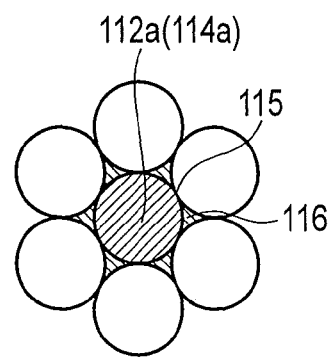
F I G. 5

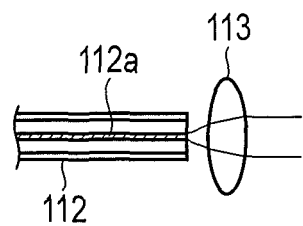
F I G. 9a
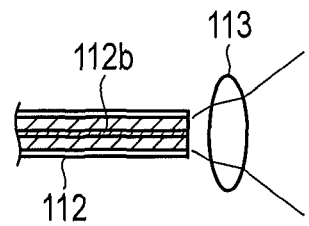
F I G. 9b
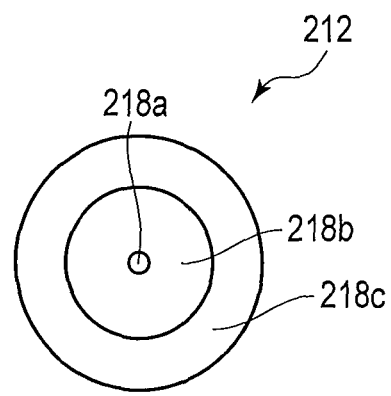
F I G. 10

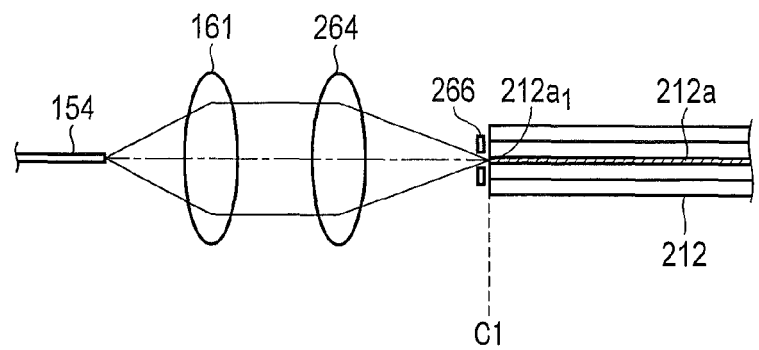
F I G. 13a
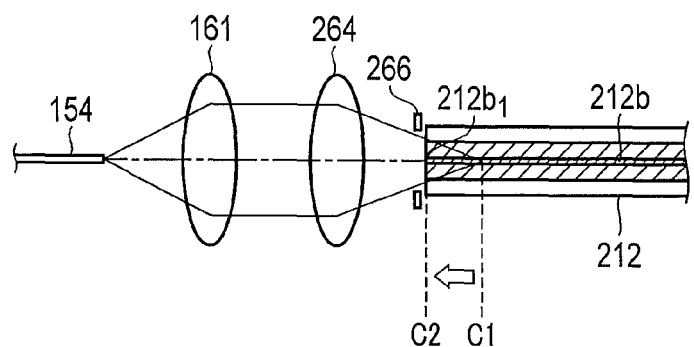
F I G. 13b
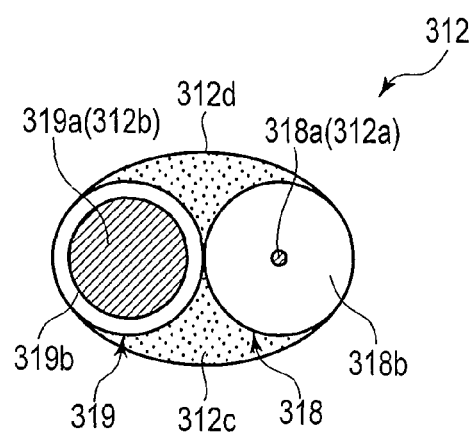
F I G. 14

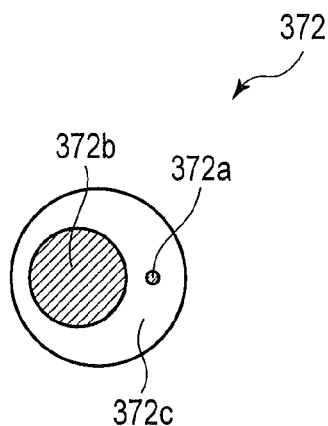
F I G. 15
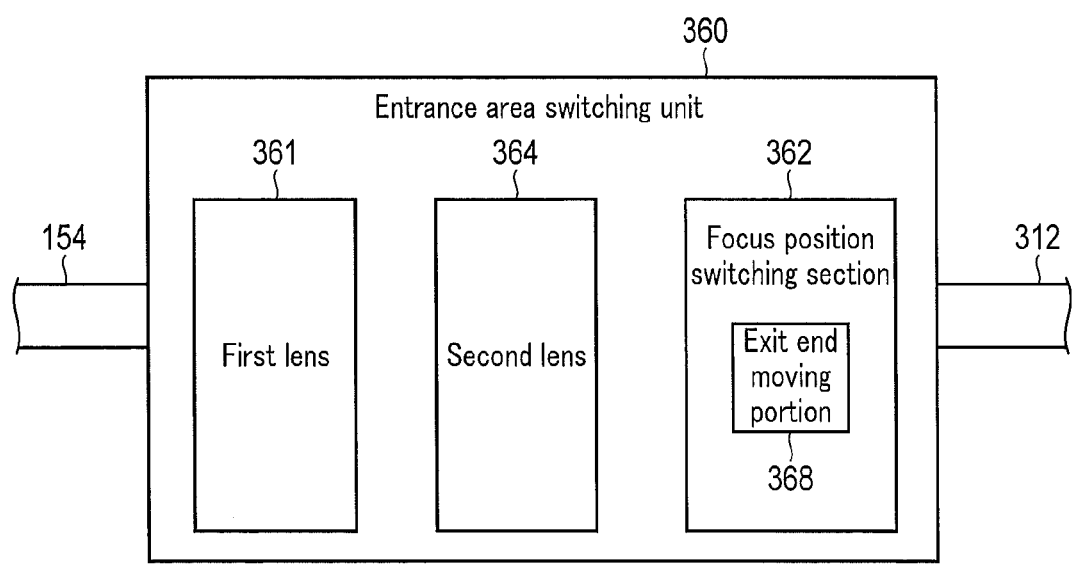
F I G. 16

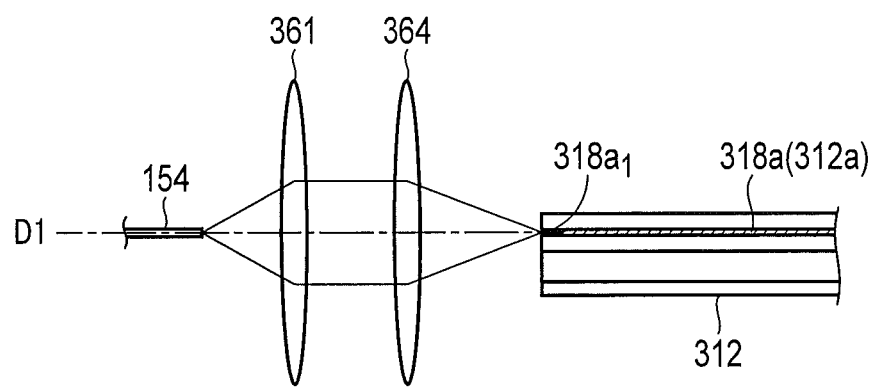
F I G. 17a
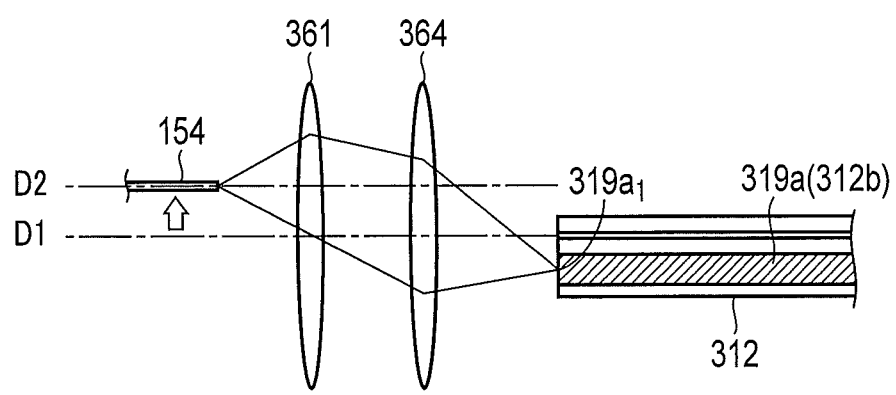
F I G. 17b

ENDOSCOPE SYSTEM

CROSS-REFERENCE TO RELATED APPLICATIONS

This application is a Continuation Application of PCT Application No. PCT/JP2015/062999, filed Apr. 30, 2015 and based upon and claiming the benefit of priority from prior the Japanese Patent Application No. 2014-100841, filed May 14, 2014, the entire contents of all of which are incorporated herein by references.

BACKGROUND OF THE INVENTION

1. Field of the Invention

The present invention relates to an endoscope system that has a plurality of observation modes making observations with lights having optical characteristics different from each other.

2. Description of the Related Art

When a coherent light, such as a laser light, is radiated to an object, phases of light scattered near a surface of the object overlap with each other, thereby forming an interference pattern called a speckle, which reflects a near-surface condition. In recent years, an optical probe has been developed to analyze living tissue based on the speckle described above which occurs when the laser light is radiated to the living tissue. For Example, Jpn. PCT National Publication No. 2004-512538 discloses an optical probe to optically analyze living tissue based on a speckle. Such an optical probe is assumed to be used together with, for example, an endoscope.

BRIEF SUMMARY OF THE INVENTION

An embodiment of the present invention is an endoscope system that has a plurality of observation modes making observations with lights having optical characteristics different from each other, the endoscope system comprising an endoscope including an insertion section provided with an illumination window; a light guide arranged in the endoscope, and including an entrance end on which the lights enter, and a plurality of light guide areas that guide the lights entered on the entrance end; and an entrance area switching unit that switches between the light guide areas, of the plurality of light guide areas, through which the entered lights are guided by switching between the areas on which the lights enter at the entrance end of the light guide in accordance with an observation mode.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram schematically showing an endoscope system of a first embodiment.

FIG. 2 is a block diagram showing a main configuration of an endoscope system.

FIG. 3 is a diagram showing in detail the endoscope system of the first embodiment.

FIG. 4a is a diagram showing an entrance end face of a bundle fiber in the first embodiment.

FIG. 4b is a diagram showing an entrance end face of a bundle fiber in the first embodiment.

FIG. 5 is an enlarged cross-sectional diagram of an entrance end face of a first light guide area of a bundle fiber in the first embodiment.

FIG. 9a is a schematic diagram showing a bundle fiber and an illumination optical system in a narrow light-distribution angle mode.

FIG. 9b is a schematic diagram showing a bundle fiber and an illumination optical system in a white light observation mode and a specific light observation mode.

FIG. 10 is a cross-sectional diagram of a double-cladding fiber in a second embodiment.

FIG. 13a is a schematic diagram showing the entrance area switching unit of the second embodiment in a speckle observation mode.

FIG. 13b is a schematic diagram showing the entrance area switching unit of the second embodiment in the white light observation mode and the specific light observation mode.

FIG. 14 is a diagram showing an entrance end face of a bundle fiber in one aspect of a third embodiment.

FIG. 15 is a diagram showing an entrance end face of a multi-core fiber in another aspect of the third embodiment.

FIG. 16 is a diagram schematically showing an entrance area switching unit in the third embodiment.

FIG. 17a is a schematic diagram showing the entrance area switching unit in the speckle observation mode.

FIG. 17b is a schematic diagram showing the entrance area switching unit in the white light observation mode and the specific light observation mode.

DETAILED DESCRIPTION OF THE INVENTION

[First Embodiment]

Figure 6:
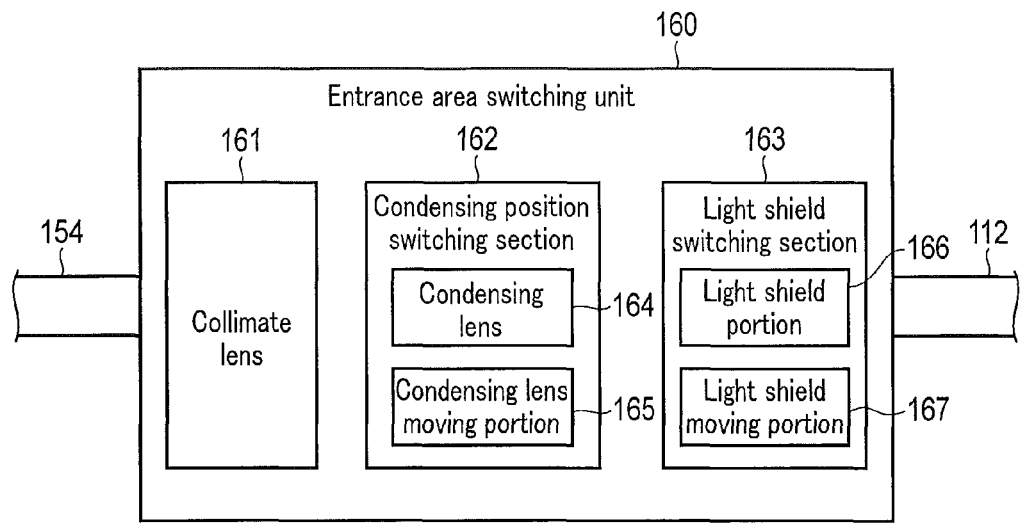
FIG. 6 is a diagram schematically showing an entrance area switching unit in the first embodiment.

An endoscope system 1 of the first embodiment of the present invention will be explained with reference to FIG. 1 to FIG. 9.

(Outline of Endoscope System)

FIG. 1 is a diagram schematically showing an endoscope system 1 of the first embodiment. The endoscope system 1 comprises an endoscope 10, an endoscope system main body (hereinafter referred to as the system main body) 100 connected to the endoscope 10, and an image display 200 connected to the system main body 100.

The endoscope 10 comprises a flexible insertion section 20 to be inserted into an insertion target, and an operation section 30 provided in a proximal end side of the insertion section 20. The insertion section 20 is an elongated tubular portion on a distal end side of the endoscope. The insertion section 20 comprises a distal rigid portion 21, a bending portion 22 provided on a proximal end side of the distal rigid portion 21, and a flexible tube portion 23 provided on a proximal end side of the bending portion 22. The distal rigid portion 21 incorporates an illumination optical system 113 including illumination lens, and an imager 121 including an observation optical system and an image sensor (see FIG. 3). The bending portion 22 bends in a desired direction by operating the operation section 30. The flexible tube portion 23 is freely bendable. For example, it bends along with a bend shape of an insertion target.

The operation section 30 comprises a main body section 31 provided on a proximal end side of the flexible tube portion 23, and a grip section 32 provided on a proximal end side of the main body section 31. The main body section 31 is provided with a treatment tool insertion port 33. A treatment tool insertion channel (not shown) extends from the treatment tool insertion port 33 to the distal rigid portion 21 through the flexible tube portion 23 and the bending portion 22. The grip section 32 includes a bending operation dial 34 to bend the bending portion 22, and a switch 35 for air supply/water supply, suction, photographing, etc.

A bundle fiber 112 for illuminating light, the fiber having a distal end connected to the illumination optical system 113 of the distal rigid portion 21, and an electric wire (an imaging cable) 123 for the image sensor, the wire having a distal end connected to the imager 121 of the distal rigid portion 21, extend inside the insertion section 20 and the operation section 30 (see FIG. 3). The bundle fiber 112 and the imaging cable 123 are housed in a universal cord 36 extending sideways from a proximal end side of the grip section 32. A connector 37 is provided at an end of the universal cord 36. The connector 37 is connected to the system main body 100.

FIG. 2 is a block diagram showing a main configuration of the endoscope system 1. FIG. 3 is a block diagram showing in detail the endoscope system 1 of the first embodiment. The endoscope system comprises an illumination device 110 that radiates an illumination light on an observation object in an insertion target, an image acquirer 120 that acquires an image of the observation object, an input section (input circuit) 130 in which an observation mode is input, a controller 140 that controls the illumination device 110 (a light source driver 111 and an entrance area switching unit 160 to be described later) and the image acquirer 120 (an image processor 122 to be described later) in accordance with observation mode information, and the above-mentioned image display 200. The illumination device 110 and the image acquirer 120 are arranged ranging from the endoscope 10 to the system main body 100. The input section 130 and the controller 140 are arranged in the system main body 100.

(Illumination Device)

The illumination device 110 comprises a light source 150, the light source driver 111, a bundle fiber 112, the entrance area switching unit 160, and the illumination optical system 113. The light source 150, the light source driver 111, and the entrance area switching unit 160 are arranged in the system main body 100. The bundle fiber 112 and the illumination optical system 113 are arranged in the endoscope 10, as described above.

(Light Source)

The light source 150 comprises a plurality of laser light sources: for example, a first laser 151a, a second laser 151b, a third laser 151c, and a fourth laser 151d. The first laser 151a is a laser that radiates a violet laser light, for example, a laser diode having a wavelength of 405 nm. The second laser 151b is a laser that radiates a blue laser light, for example, a laser diode having a wavelength of 445 nm. The third laser 151c is a laser that radiates a green laser light, for example, a laser diode having a wavelength of 515 nm. The fourth laser 151d is a laser that radiates a red laser light, for example, a laser diode having a wavelength of 635 nm.

The light source 150 further comprises a first optical fiber 152a, a second optical fiber 152b, a third optical fiber 152c, a fourth optical fiber 152d, an optical fiber combiner (an optical multiplexer) 153, and an optical fiber 154. The first to fourth optical fibers 152a to 152d and the optical fiber 154 are single fibers having a core diameter of several µm to several hundreds of µm. Proximal end sides of the first to fourth optical fibers 152a to 152d are optically connected to the first to fourth lasers 151a to 151d, respectively. Distal end sides of the first to fourth optical fibers 152a to 152d are optically connected to the optical fiber combiner 153. A distal end side of the optical fiber 154 is optically connected to the optical fiber combiner 153.

The first to fourth optical fibers 152a to 152d guide laser lights from the first to fourth lasers 151a to 151d, respectively. The optical fiber combiner 153 combines the laser lights guided through the first to fourth optical fibers 152a to 152d. The optical fiber 154 guides the light combined by the optical fiber combiner 153 to the entrance area switching unit 160.

Now, an optical coupling lens (not shown) is arranged between each of the lasers 151a to 151d and the first to fourth optical fibers 152a to 152d to converge the laser light emitted from each of the lasers 151a to 151d and couple it to the optical fibers 152a to 152d.

(Light Source Driver)

The light source driver 111 is connected to the first to fourth lasers 151a to 151d of the light source 150. Furthermore, the light source driver 111 is communicably connected to the controller 140. The light source driver 111 controls ON/OFF, driving currents, driving systems (continuous wave driving (CW), pulse driving, high-frequency superposition, etc.) of the first to fourth lasers 151a to 151d, based on control signals from the controller 140.

(Light Guide)

FIG. 4a and FIG. 4b are diagrams, each showing an entrance end face (that is, a cross section perpendicular to an optical axis) of the bundle fiber 112 as a light guide in the first embodiment. The bundle fiber 112 is provided to extend across the insertion section 20 and the operation section 30 of the endoscope 10, as schematically shown in FIG. 2 and FIG. 3.

The bundle fiber 112 in the embodiment is formed of a bundle of several tens to several thousands of optical fibers 114. Entrance ends of the optical fibers 114 are adhered to each other with an adhesive, and located on the same plane. Exit ends of the optical fibers, also adhered to each other with an adhesive, are located on the same plane. A peripheral surface of the bundle fiber 112 is covered with a protective tube. Each of the optical fibers 114 has a core diameter of several μm to several hundreds of μm. The bundle fiber 112 has a diameter of several hundreds of μm to several mm.

The bundle fiber 112 of the embodiment has a first light guide area 112a and a second light guide area 112b. The first light guide area 112a corresponds to one optical fiber 114a located at a central portion of the bundle fiber 112, as shown in FIG. 4a. The second light guide area 112b corresponds to all optical fibers 114 constituting the bundle fiber 112, as shown in FIG. 4b. In other words, the second light guide area 112b is the overall bundle fiber 112 including the first light guide area 112a. Assuming that an optical axis of the one optical fiber 114a located at the central portion of the bundle fiber 112 is an optical axis of the first light guide area and a central axis of all the optical fibers constituting the bundle fiber 112 is an optical axis of the second light guide area, the optical axis of the first light guide area and the optical axis of the second light guide area are substantially coaxial and the directions of these optical axes are equal.

The first light guide area 112a has a sectional area smaller than that of the second light guide area 112b. In the case of a light guide area having a small sectional area, phase-matched light is guided. In the case of a light guide area having a large sectional area, light of more various phases is guided. Therefore, the laser light guided through the first light guide area 112a is phase-matched light, having higher spatial coherence than that of the laser light guided through the second light guide area 112b. The degree of spatial coherence represents uniformity of a phase on a wavefront and coherence of lights on different points on a wavefront. Thus, the first light guide area 112a and the second light guide area 112b have different light guide characteristics for laser lights.

FIG. 5 is an enlarged cross-sectional diagram of an entrance end face near the first light guide area 112a of the bundle fiber 112 in the first embodiment. The one optical fiber 114a corresponding to the first light guide area 112a is coated with a coating 115, which is a breakage preventing member, so that it may be more resistant to breakage as compared to the other optical fibers constituting the bundle fiber 112. For example, the coating 115 made of polyimide is formed on the one optical fiber 114a corresponding to the first light guide area 112a, and a nylon coating is formed on the other optical fibers. Alternatively, the one optical fiber 114a corresponding to the first light guide area 112a and the other optical fibers may be coated with the same material; however, for the purpose of resistance to breakage, the coating of the one optical fiber 114a corresponding to the first light guide area 112a is thicker than that of the other optical fibers.

In a speckle observation mode (to be detailed later), heat may be generated locally near an entrance end of the optical fiber 114a corresponding to the first light guide area 112a, in which case the adhesive may burn. To avoid it, a heat generation reduction portion 116 to reduce heat generation is provided around the entrance end of the optical fiber 114a corresponding to the first light guide area 112a. The heat generation reduction portion 116 is formed by, for example, mixing a heat conductive member (a heat conductive wire, a heat conductive filler, etc.) into an adhesive, or soldering optical fibers to each other.

Although one optical fiber 114a is located in the central portion of the bundle fiber 112 corresponding to the first light guide area 112a, the number of optical fibers 114a is not limited to one, but may be two or more. However, the number of optical fibers corresponding to the first light guide area 112a is less than the number of optical fibers corresponding to the second light guide area 112b, and the laser light guided through the first light guide area 112a has spatial coherence higher than that of the laser light guided through the second light guide area 112b.

(Input Section and Observation Mode)

The endoscope system 1 has a plurality of observation modes to observe an observation object using optical characteristics different from each other. In the embodiment, the endoscope system 1 has three observation modes of: a speckle observation mode, a white light observation mode, and a specific light observation mode. In which observation mode the observation is performed (observation mode information) is input by the user to the input section 130. The input section 130 is communicably connected to the controller 140 and the input observation mode information is output to the controller 140.

The speckle observation mode is an observation mode to analyze an observation object based on a speckle that occurs in the observation object when a laser light is radiated to the observation object by the illumination device 110. In the speckle observation mode, for example, information such as a movement, shape, etc. of the observation object can be obtained by a speckle. In the embodiment, living tissue is observed based on a speckle that occurs when a violet laser light is radiated from the first laser 151a. Since a violet laser light is strongly scattered near a surface of living tissue, information on mainly a living tissue surface can be obtained.

The white light observation mode is an observation mode to observe an observation object with white light from the illumination device 110. The white light in the embodiment is generated by mixing red, green, and blue laser lights from the second laser 151b, the third laser 151c, and the fourth laser 151d.

The specific light observation mode is an observation mode to highlight a specific observation object by radiating light (specific light) having a spectrum different from that of the white light, utilizing characteristics, such as absorption, reflection, and scattering of light, in the specific observation object. In the embodiment, living tissue is observed, using specific light, that is, mixed light of the violet laser light from the first laser 151a and the green laser light from the third laser 151c. The violet laser light has a characteristic of being strongly absorbed by hemoglobin in a capillary vessel near the surface of living tissue. The green laser light has a characteristic of being strongly absorbed by hemoglobin in a thick vessel in a deep part of living tissue. From these characteristics, when an image of living tissue imaged while radiating the specific light is subjected to predetermined image processing, a capillary vessel and a thick vessel can be observed with enhanced contrast.

(Entrance Area Switching Unit)

Figure 7A:
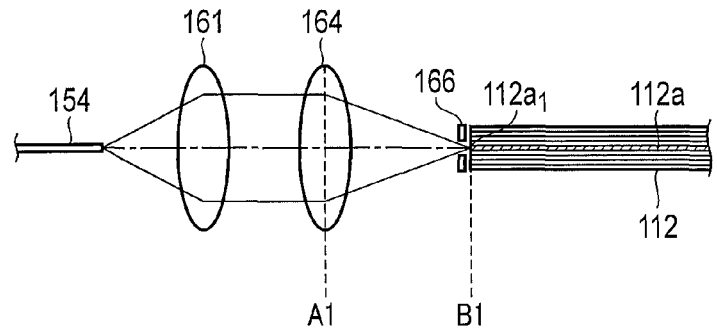
FIG. 7a is a schematic diagram showing an entrance area switching unit of the first embodiment in a speckle observation mode.
Figure 7B:
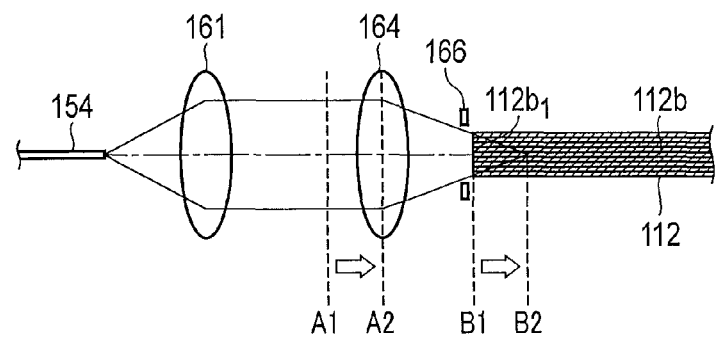
FIG. 7b is a schematic diagram showing an entrance area switching unit of the first embodiment in a white light observation mode and a specific light observation mode.

FIG. 6 is a diagram schematically showing the entrance area switching unit 160 in the first embodiment. FIG. 7a is a schematic diagram showing the entrance area switching unit 160 in the speckle observation mode. FIG. 7b is a schematic diagram showing the entrance area switching unit 160 in the white light observation mode and the specific light observation mode. The entrance area switching unit 160 comprises a collimate lens 161, a condensing position switching section 162, and a light shield switching section 163. The entrance area switching unit 160 is communicably connected to the controller 140, as shown in FIG. 2 and FIG. 3. The condensing position switching section 162 comprises a condensing lens 164 and a condensing lens moving portion 165.

The collimate lens 161 converts a laser light exiting from the optical fiber 154 of the light source 150 to a parallel light. Optical axes of the collimate lens 161 and the condensing lens 164 are positioned, as shown in FIG. 7a and FIG. 7b, to coincide with an optical axis of the optical fiber 154 of the light source 150 at an exit end and an optical axis at an entrance end of the bundle fiber 112 (=the optical axis of the first light guide area=the optical axis of the second light guide area).

The condensing lens moving portion 165 comprises, for example, a holder which holds the condensing lens 164, a guide member which guides movement of the holder, and an electric actuator which provides power to move the holder. The condensing lens 164 is movable in an optical axis direction by, for example, driving the actuator of the condensing lens moving portion 165 to move the holder along the guide member. Thus, it can change condensing positions on the optical axis. The position of the condensing lens 164 in the optical axis direction is controlled by driving the condensing lens moving portion 165 according to a control signal from the controller 140.

As shown in FIG. 7a, in the case where the condensing lens 164 is located at a position A1 on the optical axis by the controller 140, the laser light passed through the condensing lens 164 enters a first entrance area 112a1 at the entrance end face of the bundle fiber 112. The first entrance area 112a1 is an entrance end face, at which the laser light is guided through the optical fiber 114a located at the central portion of the bundle fiber 112, that is, the first light guide area 112a in the bundle fiber 112. In particular, the first entrance area 112a1 exactly includes the entrance end face of the optical fiber 114a located at the central portion of the bundle fiber 112 (see FIG. 4a). A condensing position B1 of the light passed through the condensing lens 164 is in the first entrance area 112a1 on the optical axis.

Furthermore, as shown in FIG. 7b, in the case where the condensing lens 164 is located at a position A2 on the optical axis by the controller 140, the laser light passed through the condensing lens 164 enters a second entrance area 112b1 at the entrance end face of the bundle fiber 112. The second entrance area 112b1 is an entrance end face, at which the laser light is guided through all the optical fibers 114 constituting the bundle fiber 112, that is, the second light guide area 112b in the bundle fiber 112. In particular, the second entrance area 112b1 includes the entrance end faces of all the optical fibers 114 forming the bundle fiber 112 (see FIG. 4b). A condensing position B2 of the light passed through the condensing lens 164 is nearer to the distal end side than the entrance end, so that the light can enter the bundle fiber 112 in the second entrance area 112b1.

Figure 8A:
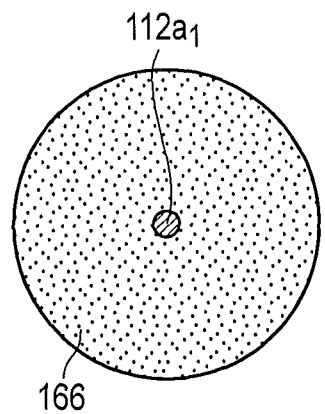
FIG. 8a is a diagram showing a light shield portion and a first entrance area of the entrance area switching unit of the first embodiment in the speckle observation mode.
Figure 8B:
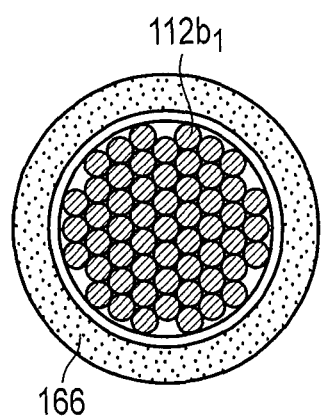
FIG. 8b is a diagram showing a light shield portion and a second entrance area of the entrance area switching unit of the first embodiment in the white light observation mode and the specific light observation mode.

FIG. 8a is a diagram showing a light shield portion 166 and the first entrance area 112a1 in the speckle observation mode. FIG. 8b is a diagram showing a light shield portion 166 and the second entrance area 112b1 in the white light observation mode and the specific light observation mode. The light shield switching section 163 can be switched between a light-shielding state (FIG. 8a) for performing light shielding of the area other than the first entrance area 112a1 and a non-light-shielding state (FIG. 8b) for not performing light shielding, so that the light passed through the condensing lens 164 can enter the first entrance area 112a1 and cannot enter the areas other than the first entrance area 112a1.

The light shield switching section 163 comprises the light shield portion 166 and a light shield moving portion 167, as shown in FIG. 6. The light shield portion 166 comprises a disk-shaped member having a central opening, and arranged in front of the entrance end face of the bundle fiber 112. The light shield portion 166 can cover and shield the entrance end face of the bundle fiber 112 from light, and only light passed through the central opening can reach the entrance end face. The light shield moving portion 167 comprises, for example, an electric actuator to change the diameter of the central opening of the light shield portion 166.

The range in which the light shield portion 166 covers the entrance end face of the bundle fiber 112 (that is, a size of the diameter of the central opening) is controlled by moving the light shield moving portion 167 according to a control signal from the controller 140. Switching of the operation of the light shield portion 166 is cooperatively controlled in association with switching between the position A1 and the position A2 of the condensing lens 164, that is, driving of the condensing lens moving portion 165 based on a control signal from the controller 140.

Now, in the embodiment, the condensing position B2 is nearer to the distal end side than the entrance end of the bundle fiber 112, so that the laser light can enter the second entrance area 112b1. However, the condensing position B2 may be nearer to the light source side than the entrance end of the bundle fiber 112.

Also, the entrance area switching unit 160 may have a configuration other than that for moving the condensing lens 164 on the optical axis, as long as the condensing positions B1 and B2 can be switched between on the optical axis. For example, a convertible lens or a lens turret including a plurality of lenses having different optical characteristics may be used. Furthermore, not only the condensing lens 164 but also the exit end of the optical fiber 154 and the collimate lens 161 may be moved together.

Furthermore, in the embodiment, the condensing position switching section 162 and the light shield switching section 163 are used together in the entrance area switching unit 160. However, the entrance area can be changed by only changing the position of the condensing lens 164 by the condensing position switching section 162, or only changing the shield range of the light shield portion 166 by the light shield switching section 163. In the case of using only the light shield switching section 163, the condensing lens 164 is fixed to the position A2.

(Illumination Optical System)

The illumination optical system 113 is a lens (lens group) that converts the laser light guided through the bundle fiber 112 to desired light distribution. The laser light, in which light distribution has been converted by the illumination optical system 113, is exited from an illumination window 117 provided at the distal end of the distal rigid portion 21 in the insertion section 20 of the endoscope 10. The laser light guided through the first light guide area 112a of the bundle fiber 112 as well as the laser light guided through the second light guide area 112b are radiated from the same illumination window 117.

(Image Acquirer)

The image acquirer 120 comprises an imager 121 placed in the insertion section 20 of the endoscope 10, and an image processor 122 placed in the system main body 100. The imager 121 and the image processor 122 are connected by the imaging cable 123 extending from the insertion section 20 through the operation section 30.

The imager 121 comprises an observation optical system including an objective lens, and an image sensor that forms an optical image acquired from the observation optical system and converts it to an electric signal. The imager 121 takes in reflected light from an observation object through the observation optical system, and picks up an image by the image sensor. The image sensor is, for example, a CCD imager or a CMOS imager. The image processor 122 performs image processing for the reflected light image acquired by the imager 121. The image processor 122 is communicably connected to the controller 140. The controller 140 controls image processing performed by the image processor 122.

(Controller)

The controller 140 receives observation mode information input to the input section 130, and controls the light source driver 111, the entrance area switching unit 160, and the image processor 122 (hereinafter referred to as objects of control). The controller 140 comprises storage 141. The storage 141 stores a control table indicating how to control the objects of control in accordance with the observation mode. The controller 140 controls the objects of control based on the control table stored in the storage 141.

Control in the speckle observation mode (control table 1) is as follows.

Control Table 1

The light source driver 111 turns on the first laser 151a (the violet laser light).

The condensing position switching section 162 of the entrance area switching unit 160 places the condensing lens 164 at the position A1 by the condensing lens moving portion 165. The light shield switching section 163 shields the area other than the first entrance area 112a1 from light with the light shield portion 166 by means of the light shield moving portion 167.

The image processor 122 performs known image processing for speckle observation.

Control in the white light observation mode (control table 2) is as follows.

Control Table 2

The light source driver 111 turns on the second laser 151b (the blue laser light), the third laser 151c (the green laser light), and the fourth laser 151d (the red laser light).

The condensing position switching section 162 of the entrance area switching unit 160 places the condensing lens 164 at the position A2 by the condensing lens moving portion 165. The light shield switching section 163 does not perform light shielding with the light shield portion 166.

The image processor 122 performs known image processing suitable for white light by mixing the second to fourth lasers 151b to 151d.

Control in the specific light observation mode (control table 3) is as follows.

Control Table 3

The light source driver 111 turns on the first laser 151a (the violet laser light) and the third laser 151c (the green laser light).

The condensing position switching section 162 of the entrance area switching unit 160 places the condensing lens 164 at the position A2 by the condensing lens moving portion 165. The light shield switching section 163 does not perform light shielding with the light shield portion 166.

The image processor 122 performs known image processing suitable for specific light observation.

(Image Display)

The image display 200 is communicably connected to the image acquirer 120 of the system main body 100. The image display 200 is, for example, a liquid crystal display, and displays an observed image created in the image acquirer 120, observation mode information, etc.

Next, an operation and a function at a time when each of the observation modes is input to the input section 130 will be described.

(Operation and Function of Speckle Observation Mode)

When the speckle observation mode is input to the input section 130, the input section 130 transmits, to the controller 140, information (input mode information) indicating that the speckle observation mode is input. The controller 140 controls the objects of control based on the control table 1 of the storage 141 upon receipt of the input mode information from the input section 130.

The light source driver 111 turns on the first laser 151a. The violet laser light emitted from the first laser 151a enters the first optical fiber 152a, thereafter guided through the optical fiber combiner 153 and the optical fiber 154, and exited from the exit end of the optical fiber 154.

The exited violet laser light is converted to parallel light by the collimate lens 161 of the entrance area switching unit 160, and thereafter condensed by the condensing lens 164 placed at the position A1. The diameter of the central opening of the light shield portion 166 is substantially the same as the diameter of the first entrance area 112a1. Thus, the second entrance area 112b1 is shielded from light by the light shield switching section 163. The violet laser light condensed by the condensing lens 164 placed at the position A1 enters the first entrance area 112a1 in the entrance end face of the bundle fiber 112, and guided through the optical fiber 114a (the first light guide area 112a) located at the central portion of the bundle fiber 112.

The guided violet laser light is converted to desired light distribution by the illumination optical system 113, and thereafter radiated through the illumination window 117 onto the observation object. The violet laser light is guided through the one optical fiber 114a, and radiated to the observation object while it maintains high spatial coherence. Therefore, a speckle occurs in the observation object.

A reflected light image of the light radiated to the observation object is picked up by the imager 121. The reflected light image acquired by the imager 121 is transmitted to the image processor 122. The image processor 122 performs predetermined (known) image processing to analyze the observation object (living tissue) based on the speckle under the control of the controller 140, and creates an image of the observation object. The image of the observation object created by the image processor 122 is displayed on the image display 200.

(Operation and Function of White Light Observation Mode)

When the white light observation mode is input to the input section 130, the input section 130 transmits, to the controller 140, information (input mode information) indicating that the white light observation mode is input. The controller 140 controls the objects of control based on the control table 2 of the storage 141 upon receipt of the input mode information from the input section 130.

The light source driver 111 turns on the second to fourth lasers 151b to 151d. The red, green, and blue laser lights respectively emitted from the second to fourth lasers 151b to 151d respectively enter the second to fourth optical fibers 152b to 152d and thereafter combined by the optical fiber combiner 153 to be a white light. Then, the white light is guided through the optical fiber 154, and exited from the exit end of the optical fiber 154.

The exited white light is converted to a parallel light by the collimate lens 161 of the entrance area switching unit 160, and thereafter condensed by the condensing lens 164 placed at the position A2 under the control of the controller 140. The white light condensed by the condensing lens 164 placed at the position A2 enters the second entrance area 112b1 at the entrance end of the bundle fiber 112, and guided through all the optical fibers 114 forming the bundle fiber 112 (the second light guide area 112b). Since the diameter of the central opening of the light shield portion 166 is larger than the diameter of the second entrance area 112b1, light shielding is not performed by the light shield switching section 163.

The guided white light is converted to desired light distribution by the illumination optical system 113, and thereafter radiated through the illumination window 117 onto the observation object. The white light is guided through several tens to several thousands of optical fibers 114, and radiated to the observation object while spatial coherence is reduced. Therefore, a speckle is reduced in the observation object.

A reflected light image of the light radiated to the observation object is picked up by the imager 121. The reflected light image acquired by the imager 121 is transmitted to the image processor 122. The image processor 122 performs predetermined (known) image processing for the white light obtained by mixing the red, green, and blue lasers, and creates an image of the observation object. The image of the observation object created by the image processor 122 is displayed on the image display 200.

(Function of Specific Light Observation Mode)

When the specific light observation mode is input to the input section 130, the input section 130 transmits, to the controller 140, information (input mode information) indicating that the specific light observation mode is input. The controller 140 controls the objects of control based on the control table 3 of the storage 141 upon receipt of the input mode information from the input section 130.

The light source driver 111 turns on the first laser 151a and the third laser 151c. The violet and green laser lights respectively emitted from the first laser 151a and the third laser 151c respectively enters the first optical fiber 152a and the third optical fiber 152c and thereafter combined by the optical fiber combiner 153. Then, the combined specific light is guided through the optical fiber 154, and exited from the exit end of the optical fiber 154.

The exited specific light is converted to parallel light by the collimate lens 161 of the entrance area switching unit 160, and thereafter condensed by the condensing lens 164 placed at the position A2. The specific light condensed by the condensing lens 164 placed at the position A2 enters the second entrance area 112b1 at the entrance end of the bundle fiber 112, and guided through all the optical fibers forming the bundle fiber 112 (the second light guide area 112b). The diameter of the central opening of the light shield portion 166 is larger than the diameter of the second entrance area 112b1. Therefore, light shielding is not performed by the light shield switching section 163.

The guided specific light is converted to desired light distribution by the illumination optical system 113, and thereafter radiated through the illumination window 117 to the observation object. The specific light is guided through several tens to several thousands of optical fibers 114, and radiated to the observation object while spatial coherence is reduced. Therefore, a speckle is reduced in the observation object.

A reflected light image of the light radiated to the observation object is picked up by the imager 121. The reflected light image acquired by the imager 121 is transmitted to the image processor 122. Utilizing the characteristics that the violet laser light is strongly absorbed by hemoglobin in a capillary vessel near the surface of the observation object (living tissue) and the green laser light is strongly absorbed by hemoglobin in a thick vessel in a deep part of the observation object (living tissue), the image processor 122 performs (known) image processing which emphasizes a contrast between the capillary vessel and the thick vessel and creates an image of the observation object. The image of the observation object created by the image processor 122 is displayed on the image display 200.

(Advantages)

According to the embodiment, the light guide areas in the bundle fiber 112 are switched by the entrance area switching unit 160. As a result, in the speckle observation mode, the laser light is guided through the first light guide area 112a of the bundle fiber 112, and in the observation modes other than the speckle observation mode, the laser light is guided through the second light guide area 112b of the bundle fiber 112. Owing to the switching, an illumination light in the observation modes can be guided through the same bundle fiber 112 and exited from the same illumination window 117. Therefore, it is possible to provide an endoscope system that can make observation with high operability without using the treatment tool insertion port 33 (the treatment tool insertion channel) of the endoscope 10. Since the bundle fiber 112 is securely placed with respect to the endoscope 10, the operation can be more stable as compared to a case where an optical probe is inserted through the treatment tool insertion port 33.

According to the embodiment, in the speckle observation mode, since the laser light is guided through the first light guide area 112a having a small cross-sectional area, the laser light is guided while high spatial coherence is maintained. Therefore, a sufficient speckle occurs in the observation object and the conventional speckle observation is possible. In the observation modes other than the speckle observation mode, since the laser light is guided through the second light guide area 112b having a large cross-sectional area, the spatial coherence of the laser light is reduced and the speckle is reduced. Therefore, in the observation modes other than the speckle observation mode, observation is possible while preventing deterioration in image quality of an image of the observation object due to unnecessary speckle.

Furthermore, due to the use of a laser having coherence as a light source, light coupling and light guide for a thin optical fiber is possible. Therefore, bright illumination can be provided while the diameter of the insertion section 20 can be reduced. Moreover, since the speckle observation and the other observations are enabled, it is possible to provide an endoscope system having high illumination performance for a plurality of observation modes.

Furthermore, the controller 140 can efficiently switch the operations of the endoscope system by cooperatively controlling the light source driver 111, the image processor 122, and the entrance area switching unit 160, based on the control table in the storage 141 in accordance with observation mode information input to the input section 130.

In addition, the condensing positions B1 and B2 are switched by the entrance area switching unit 160, thereby switching the entrance areas of the laser light with respect to the light guide and switching the light guide areas for guiding the laser light.

If the optical axes of the first light guide area and the second light guide area are the same, the light guide areas for guiding the laser light can be efficiently switched by switching the condensing positions B1 and B2 of the laser light.

According to the embodiment, in the speckle observation mode, the entrance areas other than the first entrance area are shielded from light, so that the laser light enters the first entrance area, but does not enter the entrance areas other than the first entrance area, whereas in the observation modes other than the speckle observation mode, light shielding is not performed. Thus, the light guide areas for guiding the laser light can be efficiently switched without switching optical systems.

For example, the embodiment can be efficiently realized by using a bundle fiber, a double-cladding fiber, and a multi-core fiber as a light guide. Furthermore, the breakage preventing member prevents an optical fiber included in the first light guide area of the bundle fiber from breaking, thereby preventing a defect, for example, a failure to emit an illumination light in the speckle observation mode. Moreover, the heat generation reduction portion reduces heat generation and prevents a defect such as burning, if the laser light is locally radiated to an adhesive or the like around an optical fiber included in the first light guide area in the bundle fiber.

Furthermore, in the embodiment, the optical multiplexer that combines a plurality of laser lights to a single optical beam is used. Thus, in the case where different laser lights are used in the speckle observation mode and the other observation modes, the same light guide and illumination window can be used.

According to the embodiment, the same light guide and illumination window are used in the speckle observation mode and the observation modes other than the speckle observation mode. Therefore, if the laser light used for the speckle observation mode and the laser light used for the other observation modes have the same characteristics, the same power source can be used. Accordingly, space-saving and cost-saving of the endoscope system can be facilitated.

Furthermore, in the white light observation mode, white light observation is possible by using white light obtained from laser lights of the three colors of red, green, and blue laser lights, while the effects of the laser lights are maintained. Moreover, in the specific light observation mode, a capillary vessel in a surface portion of living tissue and a thick vessel in a deep part can be observed with enhanced contrast by using violet and green laser lights.

Variants

The light source 150 is not limited to a laser light source, but may be any light source having coherence that may generate a speckle in an observation object. For example, it may be an LED. Furthermore, the optical multiplexer 153 is not limited to an optical combiner, but may be anything that performs optical multiplexing by using a spatial optical system.

The endoscope system 1 may have an observation mode other than the white light observation mode and the specific light observation mode. For example, it may have a mode for radiating a white light having a different tone, a mode for performing other known specific light observation that emphasizes an observation object, or a fluorescent observation mode in which fluorescence that appears when an observation object or pharmaceutical is radiated with excitation light is observed.

Furthermore, a plurality of observation modes may have a narrow light-distribution angle mode instead of the speckle observation mode. The narrow light-distribution angle mode is additionally used for the other observation modes.

FIG. 9a is a schematic diagram showing a bundle fiber 112 and an illumination optical system 113 in the narrow light-distribution angle mode. FIG. 9b is a schematic diagram showing the bundle fiber 112 and the illumination optical system 113 in the white light observation mode and the specific light observation mode. The illumination optical system 113 is optically designed so that light distribution conversion characteristics for a laser light guided through the first light guide area 112a and light distribution conversion characteristics for a laser light guided through the second light guide area 112b are different.

When the narrow light-distribution angle mode is input to the input section 130, the controller 140 controls the entrance area switching unit 160 so that a laser light enters the first entrance area 112a1 of the bundle fiber 112 and guided through the first light guide area 112a. In the narrow light-distribution angle mode, the light-distribution angle of illuminating light is narrower than that in the observation modes other than the narrow light-distribution angle mode. In this modification, therefore, the light distribution of illuminating light can be easily changed by switching between the light guide areas in the light guide.

[Second Embodiment]

The second embodiment of the present invention will be explained with reference to FIG. 10 to FIG. 13. In the following, the same reference numerals as used in the first embodiment will be used for the same parts, and detailed explanations thereof will be omitted, and only parts different from the first embodiment will be explained.

In the second embodiment, the light guide that guides a laser light from an entrance area switching unit 260 to an illumination optical system 113 is a double-cladding fiber 212. The entrance area switching unit 260 comprises a condensing lens 264 and an entrance end moving portion 268, instead of the condensing position switching section 162. Furthermore, the control tables in a controller 140 are changed.

(Light Guide)

Figure 11A:
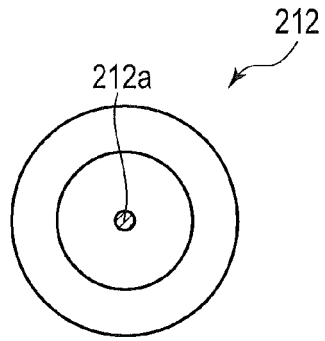
FIG. 11a is a cross-sectional diagram of a first entrance area of the double-cladding fiber in the second embodiment.
Figure 11B:
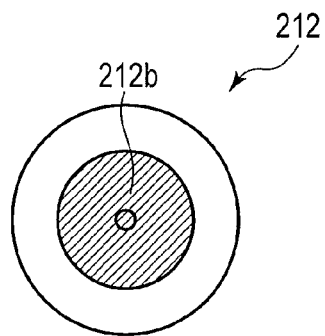
FIG. 11b is a cross-sectional diagram of a second entrance area of the double-cladding fiber in the second embodiment.

FIG. 10, FIG. 11a and FIG. 11b are cross-sectional diagrams of the double-cladding fiber 212 as a light guide in the second embodiment. The double-cladding fiber 212 comprises a central core 218a, a first cladding 218b covering a peripheral surface of the core 218a, and a second cladding 218c covering a peripheral surface of the first cladding 218b. Where the core 218a has a refractive index n1, the first cladding 218b has a refractive index n2, and the second claddings 218c has a refractive index n3, the relationship n1>n2>n3 holds. Thus, the double-cladding fiber 212 has a configuration formed of materials having three different refractive indexes which are concentrically distributed around an optical axis. The core 218a has a diameter of several μm to several tens of μm. The first cladding 218b and the second cladding 218c have a diameter of several tens of lam to several hundreds of μm.

In the double-cladding fiber 212 in the second embodiment, a first light guide area 212a corresponds to the core 218a as shown in FIG. 11a, and a second light guide area 212b corresponds to the core 218a and the first cladding 218b as shown in FIG. 11b. The first light guide area 212a has a sectional area smaller than that of the second light guide area 212b. As described before, the laser light guided through the first light guide area 212a of a small sectional area is phase-matched light, having higher spatial coherence than that of the laser light guided through the second light guide area 212b of a large sectional area.

The laser light entered on the first light guide area 212a is guided, while repeating total reflection at a boundary between the core 218a and the first cladding 218b. The laser light entered on the second light guide area 212b is guided, while repeating total reflection at a boundary between the first cladding 218b and the second cladding 218c.

(Entrance Area Switching Unit)

Figure 12:
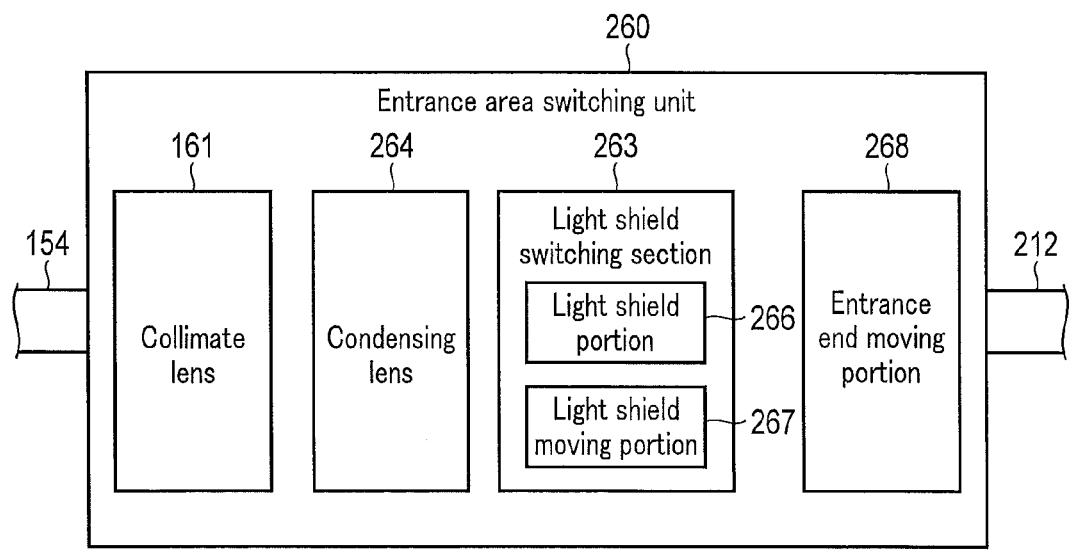
FIG. 12 is a diagram schematically showing an entrance area switching unit in the second embodiment.

FIG. 12 is a diagram schematically showing the entrance area switching unit 260 in the second embodiment. FIG. 13a is a schematic diagram showing the entrance area switching unit 260 in the speckle observation mode. FIG. 13b is a schematic diagram showing the entrance area switching unit 260 in the white light observation mode and the specific light observation mode. The entrance area switching unit 260 comprises a collimate lens 161, the condensing lens 264, a light shield switching section 263, and the entrance end moving portion 268. The entrance area switching unit 260 is communicably connected to the controller 140. The light shield switching section 263 comprises a light shield portion 266 and a light shield moving portion 267, as well as the first embodiment.

Optical axes of the collimate lens 161 and the condensing lens 264 are placed to coincide with an optical axis of the optical fiber 154 of the light source 150 at an exit end and an optical axis at an entrance end of the double-cladding fiber 212 (=the optical axis of the first light guide area=the optical axis of the second light guide area). In the embodiment, the exit end of the optical fiber 154, the collimate lens 161 and the condensing lens 264 are fixed.

The entrance end moving portion 268 moves the entrance end of the double-cladding fiber 212 in an optical axis direction. The entrance end moving portion 268 comprises, for example, a holder which holds the entrance end of the double-cladding fiber 212, a guide member which guides movement of the holder, and an electric actuator which provides power to move the holder. The double-cladding fiber 212 is movable in an optical axis direction by driving the actuator of the entrance end moving portion 268 to move the holder along the guide member. The light shield switching section 263 is also held together with the double-cladding fiber 212 and moves together with the double-cladding fiber 212.

In the embodiment, the position of the entrance end of the double-cladding fiber 212 with respect to the optical axis direction is changed by the entrance end moving portion 268 of the entrance area switching unit 260, thereby changing the entrance area of a laser light with respect to the double-cladding fiber 212. The entrance end moving portion 268 is controlled by a control signal from the controller 140.

As shown in FIG. 13a, in the case where the entrance end face of the double-cladding fiber 212 is located at a position C1 on the optical axis by the controller 140, the laser light passed through the condensing lens 264 enters a first entrance area 212a1 at the entrance end face of the double-cladding fiber 212. The first entrance area 212a1 is an entrance end face, at which the laser light is guided through the core 218a of the double-cladding fiber 212, that is, the first light guide area 212a in the double-cladding fiber 212. In particular, the first entrance area 212a1 exactly includes the entrance end face of the core 218a of the double-cladding fiber 212 (see FIG. 11a).

Furthermore, as shown in FIG. 13b, in the case where the entrance end face of the double-cladding fiber 212 is located at a position C2 on the optical axis by the controller 140, the laser light passed through the condensing lens 264 enters a second entrance area 212b1 at the entrance end face of the double-cladding fiber 212. The second entrance area 212b1 is an entrance end face, at which the laser light is guided through the core 218a and the first cladding 218b of the double-cladding fiber 212, that is, the second light guide area 212b in the double-cladding fiber 212. In particular, the second entrance area 212b1 exactly includes the entrance end face of the core 218a and the first cladding 218b of the double-cladding fiber 212 (see FIG. 11b)

(Control Table)

In the second embodiment, of the control tables stored in the storage 141 of the controller 140, control of the light source driver 111 and the image processor 122 is the same as that in the first embodiment. Therefore, only changes relating to control of the entrance end moving portion 268 and the light shield switching section 263 of the entrance area switching unit 260 will be described below.

Change of Control Table 1

In the speckle observation mode, the entrance end moving portion 268 of the entrance area switching unit 260 places the entrance end of the double-cladding fiber 212 at the position C1. The light shield switching section 263 shields the area other than the first entrance area 212a1 from light with the light shield portion 266 by means of the light shield moving portion 267.

Change of Control Table 2

In the white light observation mode, the entrance end moving portion 268 of the entrance area switching unit 260 places the entrance end of the double-cladding fiber 212 at the position C2. The light shield switching section 263 does not perform light shielding with the light shield portion 266.

Change of Control Table 3

In the specific light observation mode, the entrance end moving portion 268 of the entrance area switching unit 260 places the entrance end of the double-cladding fiber 212 at the position C2. The light shield switching section 263 does not perform light shielding with the light shield portion 266.

The embodiment can also produce the same effect as the first embodiment. If the optical axis of the first light guide area and the optical axis of the second light guide area are the same, the light guide areas for guiding the laser light can be efficiently changed by changing the end face position of the light guide in the optical axis direction.

Furthermore, the light guide area through which the laser light is guided can be changed in one optical fiber by using a double-cladding fiber as a light guide.

Note that the bundle fiber 112 may be used instead of the double-cladding fiber 212. Conversely, the double-cladding fiber 212 may be used instead of the bundle fiber 112 in the first embodiment.

[Third Embodiment]

The third embodiment of the present invention will be explained with reference to FIG. 14 to FIG. 17. In the following, the same reference numerals as used in the first embodiment will be used for the same parts, and detailed explanations thereof will be omitted, and only parts different from the first embodiment will be explained.

In the third embodiment, a light guide that guides the laser light from an entrance area switching unit 360 to an illumination optical system 113 is a bundle fiber 312 formed of a single mode fiber 318 and a multi-mode fiber 319. An exit end moving portion 368 of the entrance area switching unit 360 can change a condensing position in a direction perpendicular to an optical axis direction of the light guide. Furthermore, the control tables in a controller 140 are changed.

(Light Guide)

FIG. 14 is a diagram showing an entrance end face of the bundle fiber 312 as a light guide in the third embodiment. The bundle fiber 312 is formed of two fibers of the single mode fiber 318 and the multi-mode fiber 319. The entrance ends of these fibers, adhered to each other with an adhesive, are located on the same plane. The exit ends of these fibers, also adhered to each other with an adhesive, are located on the same plane. A peripheral surface of the bundle fiber 312 is covered with a protective tube. The multi-mode fiber has a core diameter of several tens of μm to several hundreds of μm. The single mode fiber has a core diameter of about 10 μm. Each fiber has a cladding diameter of several tens of μm to several hundreds of μm.

The single mode fiber 318 comprises a core 318a and a cladding 318b. The multi-mode fiber 319 comprises a core 319a and a cladding 319b. In the bundle fiber 312 of the third embodiment, as shown in FIG. 14, a first light guide area 312a corresponds to the core 318a of the single mode fiber 318, and a second light guide area 312b corresponds to the core 319a of the multi-mode fiber 319. The optical axis of the single mode fiber 318 (the first light guide area 312a) and the optical axis of the multi-mode fiber 319 (the second light guide area 312b) are parallel in at least the entrance end faces.

The first light guide area 312a has a sectional area smaller than that of the second light guide area 312b. As described before, the laser light guided through the first light guide area 312a of a small sectional area is phase-matched light, having higher spatial coherence than that of the laser light guided through the second light guide area 312b of a large sectional area.

Instead of the bundle fiber 312 formed of the two fibers of the single mode fiber and the multi-mode fiber, a multi-core fiber 372 as shown in FIG. 15 may be adopted. The multi-core fiber 372 comprises a first core 372a and a second core 372b independent of each other, and a cladding 372c covering the peripheral surfaces of the first core 372a and the second core 372b. Thus, one multi-core fiber having at least two independent cores for the same cladding may be used. Also in this case, the first light guide area 312a has a sectional area smaller than that of the second light guide area 312b, and the laser light guided through the first light guide area has higher spatial coherence than that of the laser light guided through the second light guide area. In the case of using a multi-core fiber, the configuration of the entrance area switching unit 360 is the same.

(Entrance Area Switching Unit)

FIG. 16 is a diagram schematically showing the entrance area switching unit 360 in the third embodiment. FIG. 17a is a schematic diagram showing the entrance area switching unit 360 in the speckle observation mode. FIG. 17b is a schematic diagram showing the entrance area switching unit 360 in the white light observation mode and the specific light observation mode. The entrance area switching unit 360 comprises a first lens 361, a second lens 364, and a condensing position switching section 362. The entrance area switching unit 360 is communicably connected to the controller 140. In the embodiment, a light shield switching section is not used.

In the embodiment, the condensing position switching section 362 comprises the exit end moving portion 368, which moves the exit end of an optical fiber 154 of a light source 150 in a direction perpendicular to optical axes direction of the first light guide area and the second light guide area. The first lens 361 and the second lens 364 are condensing optical systems which can switch a laser light in a desired entrance area. Entrance ends of the first lens 361, the second lens 364 and the bundle fiber 312 are fixed.

The exit end moving portion 368 moves the exit end of the optical fiber 154 of the light source 150 in a direction perpendicular to the optical axis of the bundle fiber 312. The exit end moving portion 368 comprises, for example, a holder which holds the exit end of the optical fiber 154, a guide member which guides movement of the holder, and an electric actuator which provides power to move the holder. The optical fiber 154 is movable in a direction perpendicular to an optical axis direction by driving the actuator of the exit end moving portion 368 to move the holder along the guide member.

In the embodiment, the positions of the exit end of the optical fiber 154 of the light source 150 in a direction perpendicular to the optical axis direction are switched between by the exit end moving portion 368 of the entrance area switching unit 360, thereby switching between the entrance areas of the laser light with respect to the bundle fiber 312. The exit end moving portion 368 is controlled by a control signal from the controller 140.

As shown in FIG. 17a, in the case where the exit end of the optical fiber 154 is located at a position D1 in a direction perpendicular to the optical axis of the bundle fiber 312 by the controller 140, the laser light enters a first entrance area 318a1 at the entrance end face of the bundle fiber 312. The first entrance area 318a1 is an entrance end face, at which the laser light is guided through the first light guide area 312a of the bundle fiber 312, that is, the core 318a of the single mode fiber 318. In particular, the first entrance area 318a1 exactly includes the entrance end face of the core 318a of the single mode fiber 318.

Furthermore, as shown in FIG. 17b, in the case where the exit end of the optical fiber 154 is located at a position D2 in a direction perpendicular to the optical axis of the bundle fiber 312 by the controller 140, the laser light enters a second entrance area 319a1 at the entrance end face of the bundle fiber 312. The second entrance area 319a1 is an entrance end face, at which the laser light is guided through the core 319a of the multi-mode fiber 319, that is, the second light guide area 312b in the bundle fiber 312. In particular, the second entrance area 319a1 exactly includes the entrance end face of the core 319a of the multi-mode fiber 319.

The first lens 361 and the second lens 364 are designed to enable the condensing position change as described above. In the embodiment, the entrance areas of the laser light with respect to the bundle fiber 312 are switched between by switching between the positions of the optical fiber 154 at the exit end in a direction perpendicular to the optical axis of the bundle fiber 312. However, while the exit end position of the optical fiber 154 is fixed, the entrance areas of the laser light with respect to the bundle fiber 312 may be switched between by means of a movable condensing optical system or a movable mirror, or the entrance end of the bundle fiber 312 may be switched between in a direction parallel to the optical axis.

(Control Table)

Of the control tables stored in the storage 141 of the controller 140 in the third embodiment, controlling of a light source driver 111 and an image processor 122 is the same as those in the first embodiment. Therefore, only changes relating to control of the exit end moving portion 368 of the entrance area switching unit 360 will be described below.

Change of Control Table 1

In the speckle observation mode, the exit end moving portion 368 of the entrance area switching unit 360 places the exit end of the optical fiber 154 at the position D1.

Change of Control Table 2

In the white light observation mode, the exit end moving portion 368 of the entrance area switching unit 360 places the exit end of the optical fiber 154 at the position D2.

Change of Control Table 3

In the specific light observation mode, the exit end moving portion 368 of the entrance area switching unit 360 places the exit end of the optical fiber 154 at the position D2.

The embodiment can also produce the same effect as the first embodiment. If the optical axes of the first light guide area and the second light guide area are parallel, the light guide areas for guiding the laser light can be efficiently switched by switching between the condensing positions of laser light in a direction perpendicular to the optical axes. In the embodiment, the exit end of the optical fiber 154 as the light guide is changed in a direction perpendicular to the optical axis direction, thereby switching between the light guide areas for guiding the laser light to the light guide having the light guide areas which are not coaxial.

Furthermore, the light guide areas for guiding the laser light can be switched between with a thin light guide by using the bundle fiber formed of the single mode fiber and the multi-mode fiber, or the multi-core fiber as the light guide.

In the embodiment, the position of the entrance end of the bundle fiber 312 is fixed, while the exit end of the optical fiber 154 is moved by the exit end moving portion 368 in a direction perpendicular to the optical axis. However, the entrance end of the bundle fiber 312 may be moved in a direction perpendicular to the optical axis by means of the entrance end moving portion 268 of the second embodiment.

The present invention is not limited to the foregoing embodiment described above, but it is evident to a person with ordinary skill in the art that various improvements and modifications can be made without departing from the subject matter of the present invention.

What is claimed is:

1. An endoscope system having a plurality of observation modes making observations with lights having optical characteristics different from each other, the endoscope system comprising:
    an endoscope including an insertion section provided with an illumination window, the endoscope having a light guide arranged in the insertion section, the light guide including an entrance end on which the lights enter, the light guide including a plurality of light guide areas for guiding the lights entered on the entrance end; and
    an entrance area switching unit that switches between the plurality of light guide areas through which the entered lights are guided by switching between areas on which the lights enter at the entrance end of the light guide in accordance with one of the plurality of observation modes,
    wherein the lights have coherence; and
    the plurality of observation modes include a speckle observation mode in which a speckle caused by the lights in the observation object is observed.

2. The endoscope system according to claim 1,
    wherein the entrance end includes a first entrance area and a second entrance area;
    the plurality of light guide areas include at least a first light guide area and a second light guide area, the first light guide area having a sectional area smaller than that of the second light guide area; and
    the entrance area switching unit switches between the light guide areas, in the speckle observation mode, the lights enter the first entrance area and guided through the first light guide area, and
    in at least one observation mode of the observation modes other than the speckle observation mode, the lights enter the second entrance area and guided through the second light guide area.

3. The endoscope system according to claim 2, further comprising:
    an input section in which the observation mode is input;
    an illumination device comprising a light source that emits the lights in accordance with the input observation mode, a light source driver that drives the light source, the entrance area switching unit, and the light guide;
    an image acquirer that acquires an image of the observation object in accordance with the observation mode; and
    a controller that cooperatively controls operations of the light source driver, the image acquirer, and the entrance area switching unit in accordance with the input observation mode.

4. The endoscope system according to claim 3, wherein the entrance area switching unit comprises a condensing optical system that condenses the lights emitted from the light source, and a condensing position switching section enabled to switch between condensing positions of the lights in accordance with control by the controller.

5. The endoscope system according to claim 4,
    wherein the condensing position switching section switches between the condensing positions of the lights to condense the lights on the entrance end of the light guide so that the lights enter the first entrance area in the speckle observation mode, and to condense the lights on a position at a predetermined distance in an optical axial direction from the entrance end of the light guide so that the lights enter the second entrance area in the observation mode other than the speckle observation mode; and
    the first entrance area is smaller than the second entrance area.

6. The endoscope system according to claim 4,
    wherein the condensing position switching section switches between the condensing positions of the lights in a direction perpendicular to an optical axis
    so that the lights enter the first entrance area in the speckle observation mode and
    the lights enter the second entrance area in the observation mode other than the speckle observation mode.

7. The endoscope system according to claim 3,
    wherein the entrance area switching unit comprises a condensing optical system that condenses the lights emitted from the light source, and an entrance end moving portion that moves the entrance end of the light guide in an optical axis direction;
    the entrance end moving portion moves the entrance end of the light guide to a condensing position of the lights so that the lights enter the first entrance area in the speckle observation mode, and moves the entrance end of the light guide to a position at a predetermined distance in the optical axial direction from the condensing position of the lights so that the lights enter the second entrance area in the observation mode other than the speckle observation mode; and
    the first entrance area is smaller than the second entrance area.

8. The endoscope system according to claim 3, wherein the entrance area switching unit comprises a light shield switching section enabled to shield against the lights in accordance with an observation mode, the light shield switching section switches to shield a part other than the first entrance area of the entrance end from the lights in the speckle observation mode, the lights enter the first entrance area and does not enter the part other than the first entrance area of the entrance end, and not to shield the entrance end from the lights in the observation mode other than the speckle observation mode.

9. The endoscope system according to claim 3, wherein spatial coherence of the illumination light guided through the first light guide area and emitted from the illumination window in the light guide is higher than spatial coherence of the illumination light guided through the second light guide area and emitted from the illumination window.

10. The endoscope system according to claim 9, wherein an optical axis of the first light guide area and an optical axis of the second light guide area are substantially coaxial.

11. The endoscope system according to claim 9, wherein the light guide is a bundle fiber formed of a bundle of a plurality of optical fibers.

12. The endoscope system according to claim 11, wherein the first light guide area and the second light guide area are determined depending on the number of optical fibers, and the number of optical fibers corresponding to the first light guide area is less than the number of optical fibers corresponding to the second light guide area.

13. The endoscope system according to claim 11,
wherein the bundle fiber comprises a bundle of at least one single mode fiber and at least one multi-mode fiber; and
the first light guide area is a core of the single mode fiber, and the second light guide area is a core of the multi-mode fiber.

14. The endoscope system according to claim 12, wherein an optical fiber included in the first light guide area comprises a breakage preventing member to provide higher resistance to breakage as compared to optical fibers other than the optical fiber included in the first light guide area.

15. The endoscope system according to claim 12, wherein a heat generation reduction member is provided near the entrance end of the bundle fiber around the optical fiber included in the first light guide area.

16. The endoscope system according to claim 9, wherein the light guide is a single optical fiber, and the single optical fiber includes the plurality of light guide areas.

17. The endoscope system according to claim 16, wherein the light guide is a double-cladding fiber comprising materials having three different refractive indexes.

18. The endoscope system according to claim 16, wherein the light guide is a multi-core fiber comprising at least two independent cores for one cladding.

19. The endoscope system according to claim 3,
wherein the light source comprises:
a plurality of light emitting portions that emit the lights having optical characteristics different from each other; and
an optical multiplexer that combines the lights emitted from the plurality of light emitting portions to a single optical beam.

20. The endoscope system according to claim 19, wherein the plurality of light emitting portions are shared by the observation modes so that the lights used in the speckle observation mode is used in the at least one observation mode other than the speckle observation mode.

21. The endoscope system according to claim 19,
wherein the plurality of light emitting portions respectively emit lights having optical characteristics different from each other to generate a white light by optical multiplexing by the optical multiplexer; and
the plurality of observation modes include a white light observation mode in which the observation object is observed by using the white light.

22. The endoscope system according to claim 1, wherein the plurality of light guide areas that have light guide characteristics different from each other with respect to the lights, that have optical axes in equal directions.

23. The endoscope system according to claim 1, wherein the lights guided through the light guide are radiated as an illumination light to an observation object through the illumination window in the observation modes.

24. An endoscope system having a plurality of observation modes making observations with lights having optical characteristics different from each other, the endoscope system comprising:
an endoscope including an insertion section, the endoscope having a light guide arranged in the insertion section, the light guide including an entrance end on which the lights enter, the light guide including a plurality of light guide areas for guiding the lights entered on the entrance end; and
a movable lens configured to move between a first position and an other position for changing a condensing position of the lights entering the light guide in accordance with one of the plurality of observation modes,
wherein the lights have coherence; and
the plurality of observation modes include a speckle observation mode in which a speckle caused by the lights in the observation object is observed.

25. The endoscope system according to claim 24, wherein in the first position, the condensing position of the lights condenses the lights on the entrance end of the light guide.

26. The endoscope system according to claim 25, wherein in the other position, the condensing position of the lights condenses the lights on a position within the light guide at a predetermined distance in an optical axial direction from the entrance end of the light guide.

* * * * *